(12) United States Patent
Lange (10) Patent No.: US 11,931,155 B2
(45) Date of Patent: *Mar. 19, 2024

(54) WEARABLE WRIST DEVICE ELECTROCARDIOGRAM

(71) Applicant: ChroniSense Medical Ltd, Yokneam (IL)

(72) Inventor: Daniel H. Lange, Kfar Vradim (IL)

(73) Assignee: ChroniSense Medical Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/127,514

(22) Filed: Mar. 28, 2023

(65) Prior Publication Data

US 2023/0233129 A1 Jul. 27, 2023

Related U.S. Application Data

(63) Continuation of application No. 14/738,636, filed on Jun. 12, 2015, now Pat. No. 11,712,190.

(51) Int. Cl.
*A61B 5/318* (2021.01)
*A61B 5/00* (2006.01)
(Continued)

(52) U.S. Cl.
CPC ............ *A61B 5/318* (2021.01); *A61B 5/0205* (2013.01); *A61B 5/02416* (2013.01);
(Continued)

(58) Field of Classification Search
CPC ........... A61B 5/318; A61B 5/30; A61B 5/316; A61B 5/0205; A61B 5/02416;
(Continued)

(56) References Cited

U.S. PATENT DOCUMENTS

| | | |
|---|---|---|
| 3,885,552 A | 5/1975 | Kennedy |
| 3,898,984 A | 8/1975 | Mandel et al. |

(Continued)

FOREIGN PATENT DOCUMENTS

| | | |
|---|---|---|
| CN | 1335756 A | 2/2002 |
| CN | 106901747 A | 6/2017 |

(Continued)

OTHER PUBLICATIONS

Arza et al., "Pulse Transit Time and Pulse Width as Potential Measure for estimating Beat-to-Beat Systolic and Diastolic Blood Pressure", Computing in Cardiology 2013, pp. 887-890.

(Continued)

*Primary Examiner* — Lynsey C Eiseman
*Assistant Examiner* — Jessandra F Hough
(74) *Attorney, Agent, or Firm* — Carr & Ferrell LLP (57) ABSTRACT

Provided are systems for measuring an electrocardiogram (ECG) using a wearable device. An example system includes the wearable device. The wearable device has a means for recording an electrical signal from a single wrist of a patient. The wearable device also has a means for detecting a pulse of the patient and recording a photoplethysmogram (PPG) signal, via a PPG optical sensor associated with the wearable device. The wearable device further has a means for generating the electrical signal segments being time-locked to the PPG signal by utilizing the PPG signal as a reference signal. Furthermore, the wearable device has a means for summing the electrical signal segments in a given time period and dividing by the number of segments to produce an average ECG waveform.

21 Claims, 6 Drawing Sheets

(51) Int. Cl.
    *A61B 5/0205* (2006.01)
    *A61B 5/024* (2006.01)
    *A61B 5/0245* (2006.01)
    *A61B 5/103* (2006.01)
    *A61B 5/11* (2006.01)
    *A61B 5/30* (2021.01)
    *A61B 5/316* (2021.01)
    *G16H 40/63* (2018.01)
    *G16H 80/00* (2018.01)

(52) U.S. Cl.
    CPC ...... *A61B 5/02427* (2013.01); *A61B 5/02438* (2013.01); *A61B 5/0245* (2013.01); *A61B 5/1032* (2013.01); *A61B 5/30* (2021.01); *A61B 5/316* (2021.01); *A61B 5/4842* (2013.01); *A61B 5/681* (2013.01); *A61B 5/6822* (2013.01); *A61B 5/6824* (2013.01); *A61B 5/6829* (2013.01); *A61B 5/721* (2013.01); *A61B 5/7239* (2013.01); *A61B 5/7275* (2013.01); *G16H 40/63* (2018.01); *G16H 80/00* (2018.01); *A61B 5/0022* (2013.01); *A61B 5/11* (2013.01); *A61B 2562/046* (2013.01); *A61B 2562/06* (2013.01)

(58) Field of Classification Search
    CPC ............ A61B 5/02427; A61B 5/02438; A61B 5/0245; A61B 5/1032; A61B 5/4842; A61B 5/681; A61B 5/6822; A61B 5/6824; A61B 5/6829; A61B 5/721; A61B 5/7239; A61B 5/7275; A61B 5/0022; A61B 7/11; A61B 2562/046; A61B 2562/06; G16H 40/63
    See application file for complete search history.

(56) References Cited

U.S. PATENT DOCUMENTS

| | | |
|---|---|---|
| 4,331,154 A | 5/1982 | Broadwater et al. |
| 4,732,158 A | 3/1988 | Sadeh |
| 4,802,486 A | 2/1989 | Goodman et al. |
| 5,050,612 A | 9/1991 | Matsumura |
| 5,316,008 A | 5/1994 | Suga et al. |
| 5,503,148 A | 4/1996 | Pologe et al. |
| 5,692,505 A | 12/1997 | Fouts |
| 5,935,060 A | 8/1999 | Iliff |
| 6,047,203 A | 4/2000 | Sackner et al. |
| 6,139,494 A | 10/2000 | Cairnes |
| 6,421,549 B1 | 7/2002 | Jacques |
| 6,527,725 B1 | 3/2003 | Inukai et al. |
| 7,142,901 B2 | 11/2006 | Kiani |
| 7,184,809 B1 | 2/2007 | Sterling et al. |
| 7,479,111 B2 | 1/2009 | Zhang et al. |
| 7,544,168 B2 | 6/2009 | Nitzan |
| 7,738,935 B1 | 6/2010 | Turcott |
| 8,172,764 B2 | 5/2012 | Gregson et al. |
| 8,602,997 B2 | 12/2013 | Banet et al. |
| 8,866,606 B1 | 10/2014 | Will et al. |
| 9,314,197 B2 | 4/2016 | Eisen |
| 10,470,692 B2 | 11/2019 | Lange et al. |
| 10,687,742 B2 | 6/2020 | Lange et al. |
| 10,952,638 B2 | 3/2021 | Lange |
| 11,160,459 B2 | 11/2021 | Gross et al. |
| 11,160,461 B2 | 11/2021 | Lange |
| 11,464,457 B2 | 10/2022 | Lange |
| 11,571,139 B2 | 2/2023 | Lange |
| 11,712,190 B2 | 8/2023 | Lange |
| 2001/0005773 A1 | 6/2001 | Larsen et al. |
| 2001/0029326 A1 | 10/2001 | Diab et al. |
| 2002/0095077 A1 | 7/2002 | Swedlow et al. |
| 2002/0133068 A1 | 9/2002 | Huiku |
| 2003/0009091 A1 | 1/2003 | Edgar, Jr. et al. |
| 2003/0036685 A1 | 2/2003 | Goodman |
| 2003/0065269 A1 | 4/2003 | Vetter et al. |
| 2003/0109776 A1 | 6/2003 | Jacques |
| 2003/0139654 A1 | 7/2003 | Kim et al. |
| 2003/0163033 A1 | 8/2003 | Dekker |
| 2004/0215095 A1 | 10/2004 | Lee et al. |
| 2005/0070775 A1 | 3/2005 | Chin et al. |
| 2005/0215913 A1 | 9/2005 | Lee et al. |
| 2005/0281439 A1 | 12/2005 | Lange |
| 2006/0074322 A1 | 4/2006 | Nitzan |
| 2006/0241510 A1 | 10/2006 | Halperin |
| 2006/0264767 A1 | 11/2006 | Shennib |
| 2007/0142720 A1 | 6/2007 | Ridder et al. |
| 2008/0214961 A1 | 9/2008 | Matsumoto et al. |
| 2008/0221419 A1 | 9/2008 | Furman |
| 2008/0255433 A1 | 10/2008 | Prough et al. |
| 2009/0024011 A1 | 1/2009 | Huiku |
| 2009/0163821 A1 | 6/2009 | Caros et al. |
| 2009/0247848 A1 | 10/2009 | Baker, Jr. |
| 2010/0016694 A1 | 1/2010 | Martin et al. |
| 2010/0179438 A1 | 7/2010 | Heneghan et al. |
| 2010/0192952 A1 | 8/2010 | Melker et al. |
| 2010/0298656 A1 | 11/2010 | McCombie et al. |
| 2010/0312079 A1 | 12/2010 | Larsen et al. |
| 2010/0324384 A1 | 12/2010 | Moon et al. |
| 2011/0060200 A1 | 3/2011 | Bernreuter |
| 2011/0066051 A1 | 3/2011 | Moon et al. |
| 2011/0077486 A1 | 3/2011 | Watson et al. |
| 2011/0082355 A1 | 4/2011 | Eisen et al. |
| 2011/0201946 A1 | 8/2011 | Turcott |
| 2011/0224564 A1 | 9/2011 | Moon et al. |
| 2011/0257551 A1 | 10/2011 | Banet et al. |
| 2012/0190944 A1 | 7/2012 | Thaveeprungsriporn et al. |
| 2012/0238834 A1 | 9/2012 | Hornick |
| 2013/0296665 A1 | 11/2013 | Kassim et al. |
| 2013/0296666 A1 | 11/2013 | Kumar et al. |
| 2013/0296673 A1 | 11/2013 | Thaveeprungsriporn et al. |
| 2013/0310700 A1 | 11/2013 | Wiard et al. |
| 2013/0338460 A1 | 12/2013 | He et al. |
| 2014/0043164 A1 | 2/2014 | Eschelman et al. |
| 2014/0142445 A1 | 5/2014 | Banet et al. |
| 2014/0142456 A1 | 5/2014 | Fischer et al. |
| 2014/0155705 A1 | 6/2014 | Papadopoulos et al. |
| 2014/0206948 A1 | 7/2014 | Romem |
| 2014/0257122 A1 | 9/2014 | Ong et al. |
| 2014/0275888 A1 | 9/2014 | Wegerich et al. |
| 2014/0278229 A1 | 9/2014 | Hong et al. |
| 2015/0109125 A1 | 4/2015 | Kaib et al. |
| 2015/0148622 A1 | 5/2015 | Moyer et al. |
| 2015/0157220 A1 | 6/2015 | Fish et al. |
| 2015/0157262 A1 | 7/2015 | Schuessler |
| 2015/0196257 A1 | 7/2015 | Yousefi et al. |
| 2015/0265161 A1 | 9/2015 | Hernandez et al. |
| 2015/0272510 A1 | 10/2015 | Chin |
| 2015/0305689 A1 | 10/2015 | Gourmelon et al. |
| 2015/0313484 A1 | 11/2015 | Burg et al. |
| 2015/0320328 A1 | 11/2015 | Albert |
| 2015/0332012 A1 | 11/2015 | Edelson et al. |
| 2015/0342538 A1 | 12/2015 | St. Pierre et al. |
| 2015/0366469 A1 | 12/2015 | Harris et al. |
| 2015/0366492 A1 | 12/2015 | De Haan et al. |
| 2015/0366518 A1 | 12/2015 | Sampson |
| 2016/0000376 A1 | 1/2016 | Murray et al. |
| 2016/0007935 A1 | 1/2016 | Hernandez et al. |
| 2016/0022220 A1 | 1/2016 | Lee et al. |
| 2016/0089033 A1 | 3/2016 | Saponas et al. |
| 2016/0093205 A1 | 3/2016 | Boyer |
| 2016/0120434 A1 | 5/2016 | Park et al. |
| 2016/0183846 A1 | 6/2016 | Derkx |
| 2016/0270668 A1 | 9/2016 | Gil |
| 2016/0270677 A1 | 9/2016 | Lin |
| 2016/0360971 A1 | 12/2016 | Gross et al. |
| 2016/0360974 A1 | 12/2016 | Lange |
| 2016/0360986 A1 | 12/2016 | Lange |
| 2016/0361003 A1 | 12/2016 | Lange et al. |
| 2016/0361004 A1 | 12/2016 | Lange et al. |
| 2017/0014037 A1 | 1/2017 | Coppola et al. |
| 2017/0156593 A1 | 6/2017 | Ferber et al. |
| 2017/0202459 A1 | 7/2017 | Cao |
| 2017/0209053 A1 | 7/2017 | Pantelopoulos et al. |

(56) References Cited

U.S. PATENT DOCUMENTS

| | | |
|---|---|---|
| 2018/0098705 A1 | 4/2018 | Chaturvedi et al. |
| 2018/0132794 A1 | 5/2018 | Lange |
| 2018/0247713 A1 | 8/2018 | Rothman |
| 2019/0015014 A1 | 1/2019 | Lange |
| 2019/0282107 A1 | 9/2019 | Gelissen |
| 2019/0298195 A1 | 10/2019 | DeGroot et al. |
| 2021/0145310 A1 | 5/2021 | Lange |
| 2021/0401313 A1 | 12/2021 | Lange |
| 2022/0265178 A1 | 8/2022 | Tran |
| 2023/0007922 A1 | 1/2023 | Lange |
| 2023/0040540 A1 | 2/2023 | Lange |
| 2023/0157572 A1 | 5/2023 | Lange |

FOREIGN PATENT DOCUMENTS

| | | |
|---|---|---|
| EP | 2430975 A1 | 3/2012 |
| EP | 3769671 A1 | 1/2021 |
| WO | WO0047108 A1 | 8/2000 |
| WO | WO2001015597 A1 | 3/2001 |
| WO | WO2006048701 A2 | 5/2006 |
| WO | WO2013061415 A1 | 5/2013 |
| WO | WO2014022906 A1 | 2/2014 |
| WO | WO2015047015 A1 | 4/2015 |
| WO | WO2015197383 A1 | 12/2015 |
| WO | WO2017079828 A1 | 5/2017 |
| WO | WO2017140696 A1 | 8/2017 |
| WO | WO2017141131 A1 | 8/2017 |
| WO | WO2018085563 A1 | 5/2018 |

OTHER PUBLICATIONS

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

Gözde, Ateç et al., "Measuring of Oxygen Saturation Using Pulse Oximeter Based on Fuzzy Logic," Medical Measurements and Applications Proceedings (MEMEA), 2012 IEEE International Symposium, May 18, 2012, pp. 1-6.

Sam et al., "Feasibility of single-arm single-lead ECG biometrics", 22nd European Signal Processing Conference (EUSIPCO), Sep. 1, 2014, pp. 2525-2529.

Zhang et al., "Theoretical Study on the Effect of Sensor Contact Force on Pulse Transmit Time", IEEE Transactions on Biomedical Engineering, Sep. 2007, 10 pages.

Farki et al., "A Novel Clustering-based Algorithm for Continuous and Noninvasive Cuff-less Blood Pressure Estimation," Journal of Healthcare Engineering, vol. 2022, Jan. 15, 2022, 13 pages.

FIG. 6

WEARABLE WRIST DEVICE ELECTROCARDIOGRAM

CROSS-REFERENCE TO RELATED APPLICATIONS

The present application is a continuation of and claims priority benefit of U.S. patent application Ser. No. 14/738,636, filed Jun. 12, 2015, entitled "Wearable Device Electrocardiogram." The present application is also related to U.S. patent application Ser. No. 14/738,666 titled "Monitoring Health Status of People Suffering from Chronic Diseases" filed on Jun. 12, 2015 and U.S. patent application Ser. No. 14/738,711 filed on Jun. 12, 2015. The subject matter of the aforementioned applications is incorporated herein by reference for all purposes.

FIELD

The present application relates to systems and methods for monitoring health status of people suffering from chronic diseases, and more specifically to measuring an electrocardiogram (ECG) with a wearable device.

BACKGROUND

It should not be assumed that any of the approaches described in this section qualify as prior art merely by virtue of their inclusion in this section.

An ECG represents electrical activity of a heart. Traditionally, an ECG is recorded by placing surface electrodes at multiple locations of a patient's body (for example, 12 locations in a 12-lead system).

An ECG is used to measure the heart's electrical activity, generated by the polarization and depolarization of cardiac tissue, and to translate such electrical activity into an electrical waveform. The ECG waveform can provide information concerning the rate and regularity of heartbeats; size and position of the chambers, and can indicate the presence of damage to the heart muscle. The ECG waveform measurements can be used to analyze the effects of drugs or devices, such as, for example, the effect of a beta-blocker medication on cardiac arrhythmia pathologies, or the effect of a pacemaker, used to regulate the heart.

The ECG waveform can often detect heart disease, heart attack, an enlarged heart, or abnormal heart rhythms that may cause heart failure. Particularly, certain changes in the ECG waveform may be indicative of life-threatening medical conditions, such as, for example, a myocardial infarction, an acute coronary ischemia, a ventricular hypertrophy, a pulmonary embolism, and so forth.

In clinical settings, multiple channels can be used to capture different vectors of electrical activity of a beating heart. Monitoring patients out of hospital using a one-lead electrocardiography has proved to provide valuable health status information. Monitoring chronically ill patients outside a hospital environment is crucial for detecting early onset of symptoms and negative progression of chronic diseases.

Some existing wearable ECG systems include sensing capabilities embedded in vests or shirts. Existing wearable devices wearable are generally designed for measuring heart rates during exercise and do not provide sophisticated analysis of heart activity. Furthermore, while making ECG measurements from a wrist, ankle, or neck is possible, it generally requires closing an electric circuit around the heart using another body part. For example, a patient may be required to close the electric circuit by touching a wrist worn device with the other hand. The requirement of the patient's active participation in the measurement process can limit the practical usability of the wearable device.

Therefore, a need exists to receive ECG measurements using a wearable device without requiring the patient to take an active role in the measurement process.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one aspect of the present disclosure, a system for measuring ECG data using a wearable device is provided. The wearable device can include at least one electrical sensor. The wearable device can be configured to record, via the at least one electrical sensor, an electrical signal from a wrist of a patient. It should be noted, however, that the embodiments of the present disclosure are not limited to the wrist and other parts of a human body such as ankles or neck can be used. The electrical signal can include an ECG signal and a noise. The wearable device can be further operable to split the electrical signal into segments based on a reference signal. The reference signal can include an indication of onset times of heart beats, or other fiducial timing information relating to heart beat. The wearable device can be further operable to average the segments to derive an average ECG data.

The wearable device can further include an optical sensor. The optical sensor can be operable to measure a color of skin beneath a pulsating artery of the wrist. In certain embodiments, the reference signal is a photoplethysmogram (PPG) signal recorded via the optical sensor simultaneously with the electrical signal. In some embodiments, the reference signal is a first derivative of a PPG signal recorded via the optical sensor simultaneously with the electrical signal.

In various embodiments, prior to the averaging, the segments are distributed into groups. Each group can include segments corresponding to a certain heart rate. The averaging can include averaging segments belonging to at least one of the groups.

In some embodiments, the electronic sensor includes a first input plate disposed at a proximity of an inner side of a wrist and a second input plate disposed at a proximity of an outer side of the wrist. In certain embodiments, the electronic sensor includes two input plates located on opposite sides of the wrist.

The wearable device is most commonly embodied in the form of a wristband, a watch, or a bracelet configured to be worn on the wrist. The device may be configured to be worn on any other suitable part of the body of the user.

The wearable device is configured to analyze average ECG data recorded over an extended period of time to determine trends in parameters of the average ECG data. The wearable device can be further operable to determine, based at least on the trends, at least one possible symptom or a probable progression of at least one chronic heart disease. The wearable device can be configured to provide reports and warning messages regarding the at least one possible symptom and the probable progression. In some embodiments, the segments are intervals between two subsequent heart beats.

According to another aspect of the present disclosure, the wearable device includes means for recording, via at least a first input plate and a second input plate of at least one electrical sensor associated with the wearable device, an electrical signal from a single wrist of a patient, the electrical signal including an ECG component and a noise component, wherein the first input plate and the second input plate are placed in contact with opposite sides of the single wrist of the patient. The wearable device also includes means for detecting a pulse of the patient and recording a photoplethysmogram (PPG) signal, via a PPG optical sensor associated with the wearable device, the electrical signal and the PPG signal being simultaneously measured at the single wrist of the patient. The wearable device further includes a means for generating, from the recorded electrical signal, electrical signal segments of the recorded electrical signal, the electrical signal segments being time-locked to the PPG signal by utilizing the PPG signal as a reference signal. Finally, the wearable device includes a means for summing the electrical signal segments in a given time period and dividing by the number of segments to produce an average ECG waveform based on a subset of the electrical signal segments, resulting in a reduction of the uncorrelated noise component of the electrical signal and an extraction of the average ECG waveform from the electrical signal during the time period.

According to another example embodiment of the present disclosure, a system for measuring an electrocardiogram (ECG) using a wearable device comprises the wearable device including at least one electrical sensor. The wearable device is configured to record, via at least a first input plate and a second input plate of the at least one electrical sensor associated with a wearable device, an electrical signal from a single wrist of a patient, the electrical signal including an ECG component and a noise component, wherein the first input plate and the second input plate are placed in contact with opposite sides of the single wrist of the patient. The wearable device is also configured to detect a pulse of the patient and recording a photoplethysmogram (PPG) signal, via a PPG optical sensor associated with the wearable device. The electrical signal and the PPG signal are simultaneously measured at the single wrist of the patient. The wearable device is further configured to generate, by a processor from the recorded electrical signal, electrical signal segments of the recorded electrical signal. The electrical signal segments are time-locked to the PPG signal by utilizing the PPG signal as a reference signal. Furthermore, the wearable device is configured to sum the electrical signal segments in a given time period and divide by the number of segments to produce an average ECG waveform based on a subset of the electrical signal segments, resulting in a reduction of the uncorrelated noise component of the electrical signal and an extraction of the average ECG waveform from the electrical signal during the time period.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for measuring ECG data using a wearable device. Embodiments of the present disclosure can allow measuring ECG data of a patient in a non-intrusive manner while, for example, the patient is at home, at work, outdoors, traveling, or is located at some other stationary or mobile environment. Some embodiments of the present disclosure include the wearable device that the patient wears around a wrist. The wearable device allows measuring ECG data from a wrist of the patient without requiring the patient to take an active role in the process. The ECG data collected during an extended period of time can be analyzed to detect and track trends and to make conclusions concerning symptoms and a progression of one or more chronic diseases from which the patient might suffer.

According to some example embodiments, a method for measuring ECG data using a wearable device includes recording an electrical signal from a patient's wrist. The electrical signal can be recorded via at least one electrical sensor associated with the wearable device. The electrical signal can include an ECG signal and a noise. The method allows splitting the electrical signal into segments. The splitting can be based on a reference signal. The reference signal can include an indication of onset times of heart beats. The method can include averaging the segments to derive average ECG data.

Figure 1:
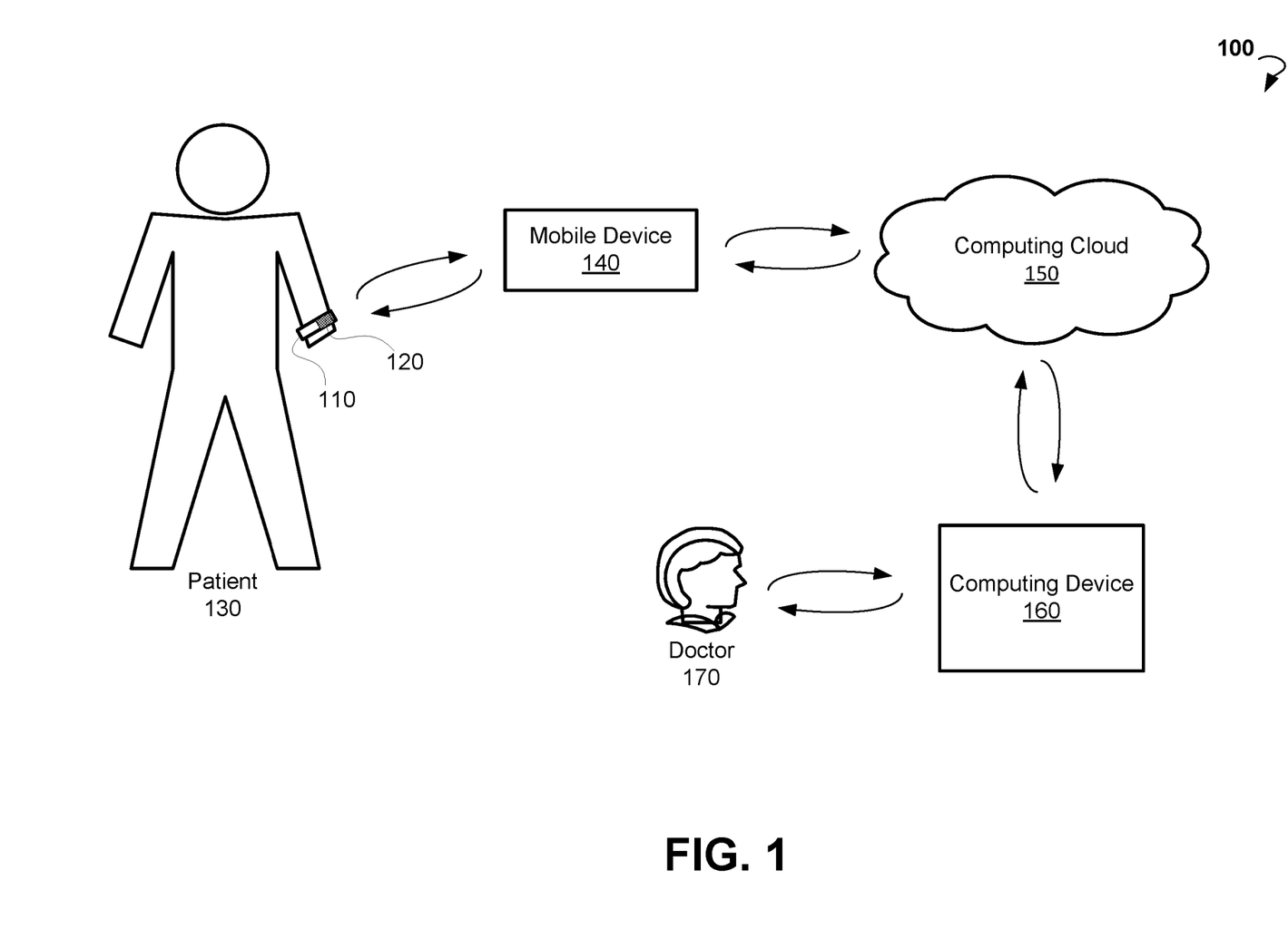
FIG. 1 is a block diagram showing an example system for measuring ECG data using a wearable device.

Referring now to FIG. 1, an example system 100 for measuring ECG data using a wearable device is shown. The system 100 includes at least the wearable device 110. The wearable device can include sensors 120. In some embodiments, the wearable device 110 is worn by a patient 130 (for example, on a wrist) for an extended period of time. The wearable device 110 can be carried out as a watch, a bracelet, a wristband, and the like.

The wearable device 110 can be operable to constantly collect, via sensors 120, sensor data from a patient 130.

Based on the sensor data, the wearable device 110 can be operable to obtain ECG data associated with the patient 130.

In some embodiments, the system 100 includes a mobile device 140. The mobile device 140 can be communicatively coupled to the wearable device 110. In various embodiments, the mobile device 140 is operable to communicate with the wearable device 110 via a wireless connection. The mobile device 140 can include a mobile phone, a smart phone, a phablet, a tablet computer, a notebook, and so forth. The mobile device 140 can be operable to receive the sensors data and analyze the sensor data to generate ECG data.

In further embodiments, the system 100 may include a cloud-based computing resource 150 (also referred to as a computing cloud). In some embodiments, the cloud-based computing resource 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data to the computing cloud 150 for further analysis (for example, for extracting ECG data from the sensor data and storing the results). The computing cloud 150 can be operable to run one or more applications and to provide reports regarding health status of the patient, based on trends in ECG data over time. A doctor 170 treating the patient 130 may access the reports (for example, via computing device 160) using the Internet or a secure network. In some embodiments, the results of the analysis of the medical parameters can be sent back to the mobile device 140.

Figure 2:
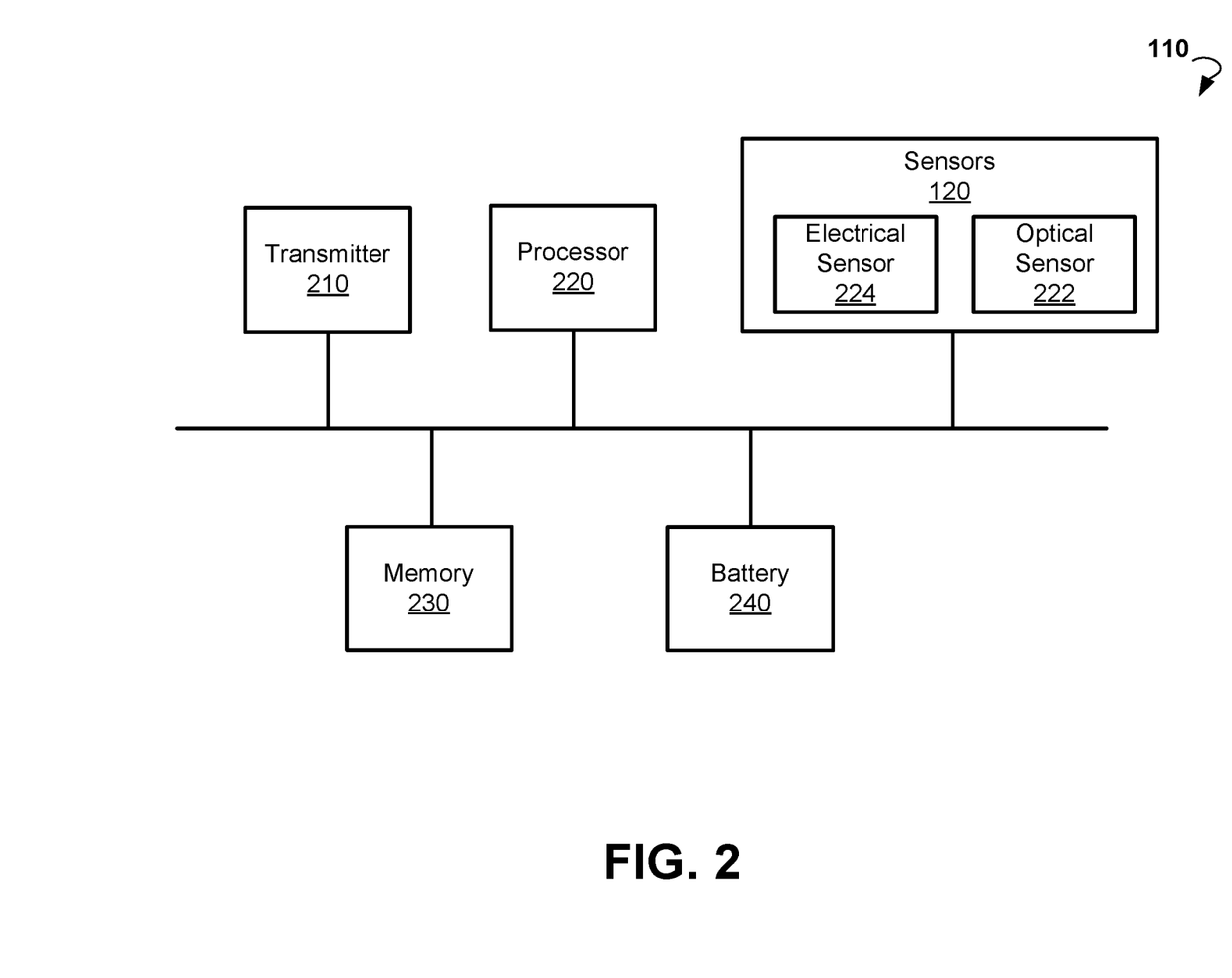
FIG. 2 is a schematic diagram showing components of an example device for measuring ECG data using the wearable device.

FIG. 2 is a block diagram illustrating components of wearable device 110, according to an example embodiment. The example wearable device 110 includes sensors 120, a transmitter 210, a processor 220, memory 230, and a battery 240. The wearable device 110 may comprise additional or different components to provide a particular operation or functionality. Similarly, in other embodiments, the wearable device 110 includes fewer components that perform similar or equivalent functions to those depicted in FIG. 2.

The transmitter 210 can be configured to communicate with a network such as the Internet, a Wide Area Network (WAN), a Local Area Network (LAN), a cellular network, and so forth, to send data streams (for example sensor data, ECG data, and messages).

The processor 220 can include hardware and/or software, which is operable to execute computer programs stored in memory 230. The processor 220 can use floating point operations, complex operations, and other operations, including processing and analyzing sensor data, to extract ECG data.

In some embodiments, the battery 240 is operable to provide electrical power for operation of other components of the wearable device 110. In some embodiments, the battery 240 is a rechargeable battery. In certain embodiments, the battery 240 is recharged using an inductive charging technology.

In various embodiments, the sensors 120 include at least one electrical sensor 224 and at least one optical sensor 222. In certain embodiments, the sensor 120 can include position and motion sensors. The motion sensors can include an accelerometer, gyroscope, and Inertial Measurement Unit (IMU).

Figure 3A:
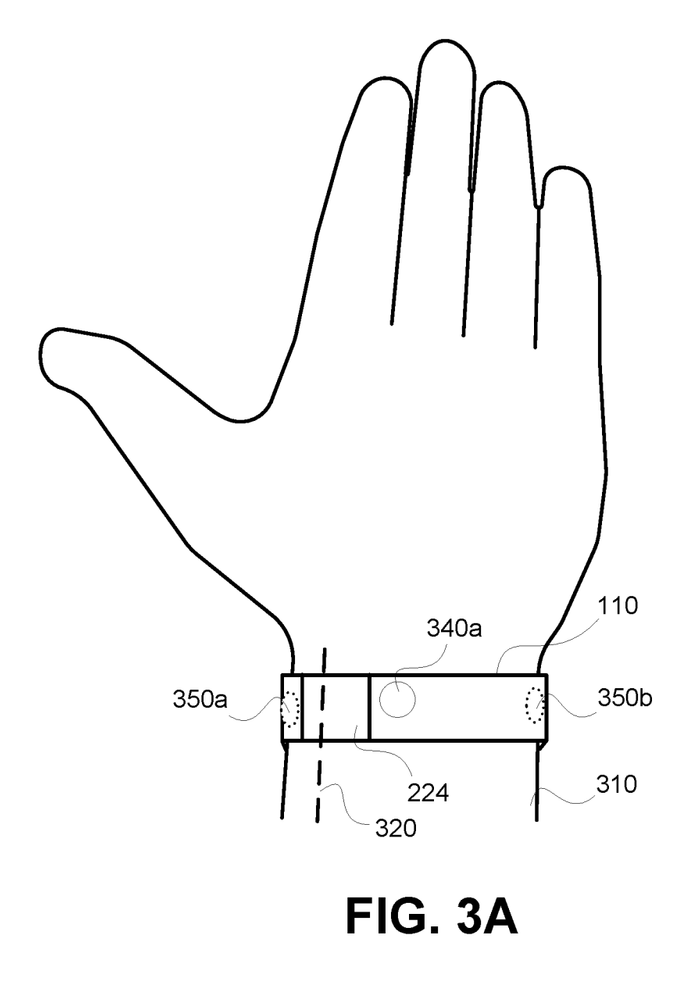
FIG. 3A is a schematic diagram illustrating an example device for measuring ECG data using the wearable device.

FIG. 3A is a schematic diagram illustrating an example wearable device 110 placed around the left wrist 310 of a patient. In the example of FIG. 3A, the wearable device 110 is carried in a shape of a watch, a ring and/or a bracelet.

The electrical sensor 224 can include a differential amplifier operable to measure the electrical signal from the wrist 310. The electrical sensor 224 can include two active amplifier input plates embedded in the wearable device at opposite ends. In some embodiments, the first input plate (not shown) can be placed above the outer side of the wrist, and the second input plate 340a can be placed beneath the inner side of the wrist 310. Alternatively or additionally, in other embodiments, the input plates 350a and 350b can be placed in contact with, respectively, the left and right sides of the wrist 310.

In some embodiments, the optical sensor 222 can be placed beneath a pulsating artery travelling along the arm and into the wrist 310. In some embodiments, the radial artery 320 passing in the inner wrist is used for measurements by the optical sensor 222. In other embodiments, other arteries such as the ulnar artery may be used. An external light source generating constant lighting can be used to radiate the pulsating artery. A beam reflected form the pulsating artery can be intercepted by the optical sensor 222. In certain embodiments, red lighting is used to radiate the pulsating artery. Alternatively, in other embodiments, other lighting, for example white lighting, can be used.

Figure 3B:
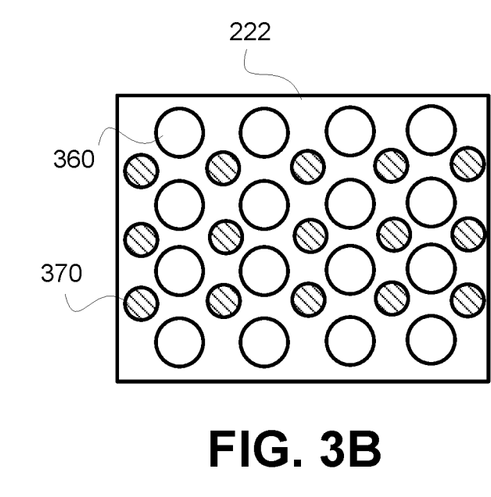
FIG. 3B is a block diagram showing an example optical sensor.

FIG. 3B is a schematic diagram showing an optical sensor 222, according to an example embodiment. The optical sensor 222 can include multiple light sensors 360 (for example, photoelectric cells) to measure the reflected light. The pulsating artery can be irradiated by multiple light transmitters 370 (for example, Light Emission Diodes (LEDs)). The number and location of the light sensors and light transmitters can be chosen in a way that if, accidently, the wearable device 110 slides off, at least one of the light sensors is still located sufficiently close to the pulsating artery. In some embodiments, when measuring the light reflected from the pulsating artery, a signal from those photoelectric cells that provides the strongest output can be selected for further processing.

Figure 4:
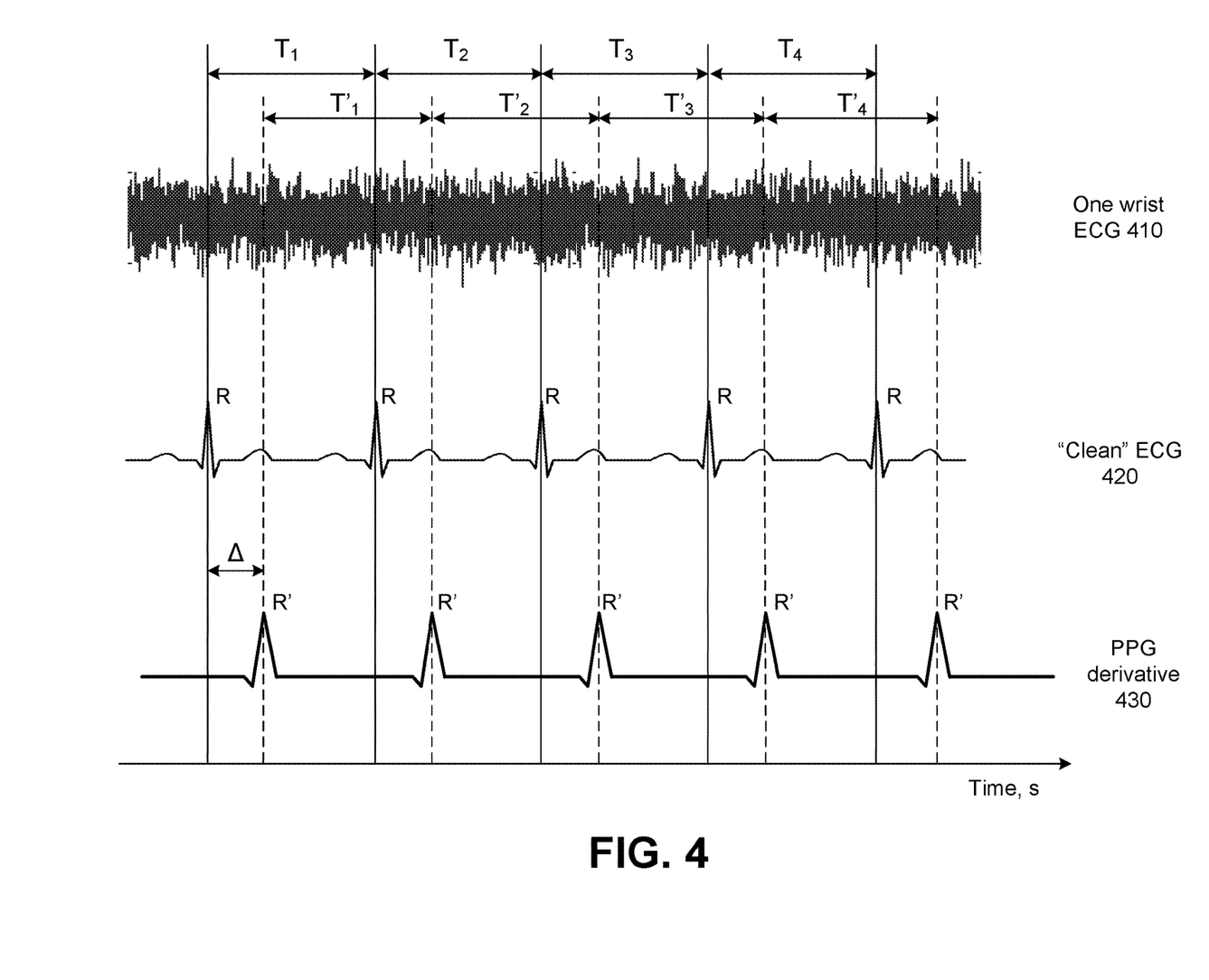
FIG. 4 shows example plots of noisy ECG a data, a "clean" ECG waveform, and a PPG derivative.

FIG. 4 shows plots of an example electrical signal 410 measured from one wrist (or some other limb), an example plot of "clean" ECG signal 420, and a plot of first derivative 430 of a PPG signal. The electrical signal can be recorded with electrical sensor 224 using input plates placed on the wearable device 110. Taking measurement from a single hand or a single wrist can be challenging because the difference in voltages between measured locations is miniscule. The electrical signal 410 measured at the wrist can include an ECG signal and a noise. The noise can be caused by muscle activity, patient movements, and so forth. The noise component can be larger than the ECG signal. In some embodiments, the signal-to-noise ratio (SNR) is in the range of −40 dB to −60 dB.

The "clean" ECG signal 420 is an imaginary ECG signal that can be obtained simultaneously with electrical signal 410 using a regular two leads ECG recording, for example, when two input plates of a cardiograph are placed at two different wrists of the patient. The "clean" ECG signal 420 can include R peaks corresponding to heart beats. Using the "clean" ECG signal 420 as a reference, the electrical signal 410 can be split in segments, with each of the segments $T_i$ (i=1, 2, 3 . . . ) corresponding to one RR interval (an interval between two successive heart beats). Each segment $T_i$ (i=1, 2, 3 . . . ) of an electrical signal can contain an ECG signal $s_i(t)$ and a noise component $e_i(t)$. Assuming a stationary heartbeat waveform, if segments $T_i$ (i=1, 2, 3 . . . ) are substantially of the same length, then signal $s_i(t)$ is substantially of the same waveform when noise components $e_i(t)$ are not correlated to each other. The following averaging technique can be used to extract an ECG signal S(t) from electrical signal 410:

$$S(t) = \sum_{i=1}^{p}(s_i(t) + e_i(t)),$$

wherein p is a number of segments $T_i$ (i=1, 2, 3 . . . ) selected for averaging. The segments $T_i$ (i=1, 2, 3 . . . ) selected for averaging are measured for a pre-determined time period (for example, for a few seconds or a few minutes). The segments selected for averaging are substantially of the same length.

The averaging increases the SNR in resulting average ECG signal S(t). In certain embodiments, the SNR in resulted averaged ECG signal S(t) can be further increased by weighted averaging, Wiener filtering, Adaptive filtering, and with other techniques.

Since the "clean" ECG signal 420 is not available when the measurements are carried out on a single wrist, a PPG signal can be used as a reference signal to split the electrical signal 410 in segments. In various embodiments of the present disclosure, the PPG signal is recorded using the optical sensor 222 simultaneously with the electrical signal 410, which is recorded by the electrical sensor 224. The PPG signal is obtained by sensing a change in the color of skin. The change of the skin color is caused by a blood flow in the pulsating artery. In some embodiments, the first derivative 430 of PPG can be used as a reference signal. The first derivative 430 of PPG signal can include sharp peaks R' corresponding to the heart beats. Since it takes a time for blood to flow from the heart to the wrists, the peaks R' are shifted by a time period A relative to the heart beats R in "clean" ECG signal 420. Assuming that A is approximately the same for all heart beats, the peaks R' can be used to split the electrical signal 410 in segments $T'_i$ (i=1, 2, 3 . . . ). In some embodiments, the averaging technique can be applied to segments $T'_i$ (i=1, 2, 3 . . . ) of ECG data to increase SNR. In other embodiments, the segments $T'_i$ (i=1, 2, 3 . . . ) can be shifted by the time period A and the averaging can be applied to the shifted segments.

In some embodiments, prior to the averaging, the segments of the ECG signal can be split into groups. Each of these groups can include segments of the ECG signal corresponding to a certain pulse rate at which the segments were measured. The pulse rate is provided based on measurements of the PPG signal. The averaging can be applied to each group of segments independently.

In some embodiments, averaging can be performed on ECG data collected within a pre-determined period of time (for example, during a day). The average ECG data that is obtained by averaging segments collected during a day can be further compiled and saved locally (in the memory of wearable device 110 or mobile device 140) or remotely (in a memory storage of computing cloud 150) for further analysis. The average data can be analyzed to detect and track changes and trends in average ECG data over an extended period of time. The extended period of time can include one or more weeks, one or more months, or even years.

In some embodiments, based at least on the trends, symptoms of one or more chronic diseases are indicated due to their relationship with measured or derived parameters. In certain embodiments, reports concerning suspected progression of one or more chronic diseases can be generated based on the trends. In some embodiments, based on the symptoms, the patient can be advised to take palliative steps such as taking a medication and/or to contact a medical professional.

In various embodiments, processing electrical signal 410 and first derivative 430 of PPG signal, analyzing average ECG data to detect and track trends, and generating reports on symptoms and progression of chronic diseases can be performed locally on wearable device 110 and/or mobile device 140 and remotely in computing cloud 150.

It may be desirable to utilize the motion data obtained via the motion sensors to provide parameters of body movement and tremor. In certain embodiments the motion data can be used for performing a noise analysis to remove artifacts in ECG data.

In further embodiments, an accelerometer (a tri-axis accelerometer) can be placed on skin near an artery of the patient and provide data on flexion of the artery due to blood flow. The data provided by the accelerometer can be used to generate the ECG data.

The wearable device 110 can be configured to operate in at least two modes. A first mode can include reading an ECG data from one wrist, synchronizing the ECG data with reference PPG data, segmenting and grouping the ECG data to perform averaging ECG data to improve the SNR.

In a second mode, the wearable device can be configured to improve the PPG data based on ECG data as a reference signal. While operating the wearable device in the second mode, the patient can be asked to touch the wearable device with other hand, in order to allow receiving a "two-handed" ECG data (good quality ECG data) which include much less noise than "a single wrist" ECG data. The wearable device can include an extra lead to receive input from other hand when touching. In the second mode, poor PPG data can be segmented using the "two-handed" ECG data as a reference signal. The PPG segments can be dropped and averaged to receive high quality PPG data. The high quality PPG data can be used along with good quality ECG data to estimate, for example, a pulse travel time.

In some embodiments, the system 100 for measuring ECG data includes at least one additional wearable device. The additional wearable device can be identical to the wearable device 110. In some embodiments, patient 130 may wear one of the devices throughout the day and another device at nighttime. In certain embodiments, the wearable device can be changed when the battery level drops below a certain level. The wearable device that is not in use at the moment can be recharged. In some further embodiments, the device can be recharged using induction charging technology. In some embodiments, since both the devices are in communication with mobile device 140, the replaced device can, at least partially, transmit recorded information (ECG data and PPG data) to the replacing wearable device for synchronization. The information can be downloaded to the mobile device 140 and the mobile device 140 can be operable to send the information to the replacing device. Additionally in other embodiments, the two wearable devices can be configured to exchange information (for example ECG data and PPG data) via the computing cloud 150.

Figure 5:
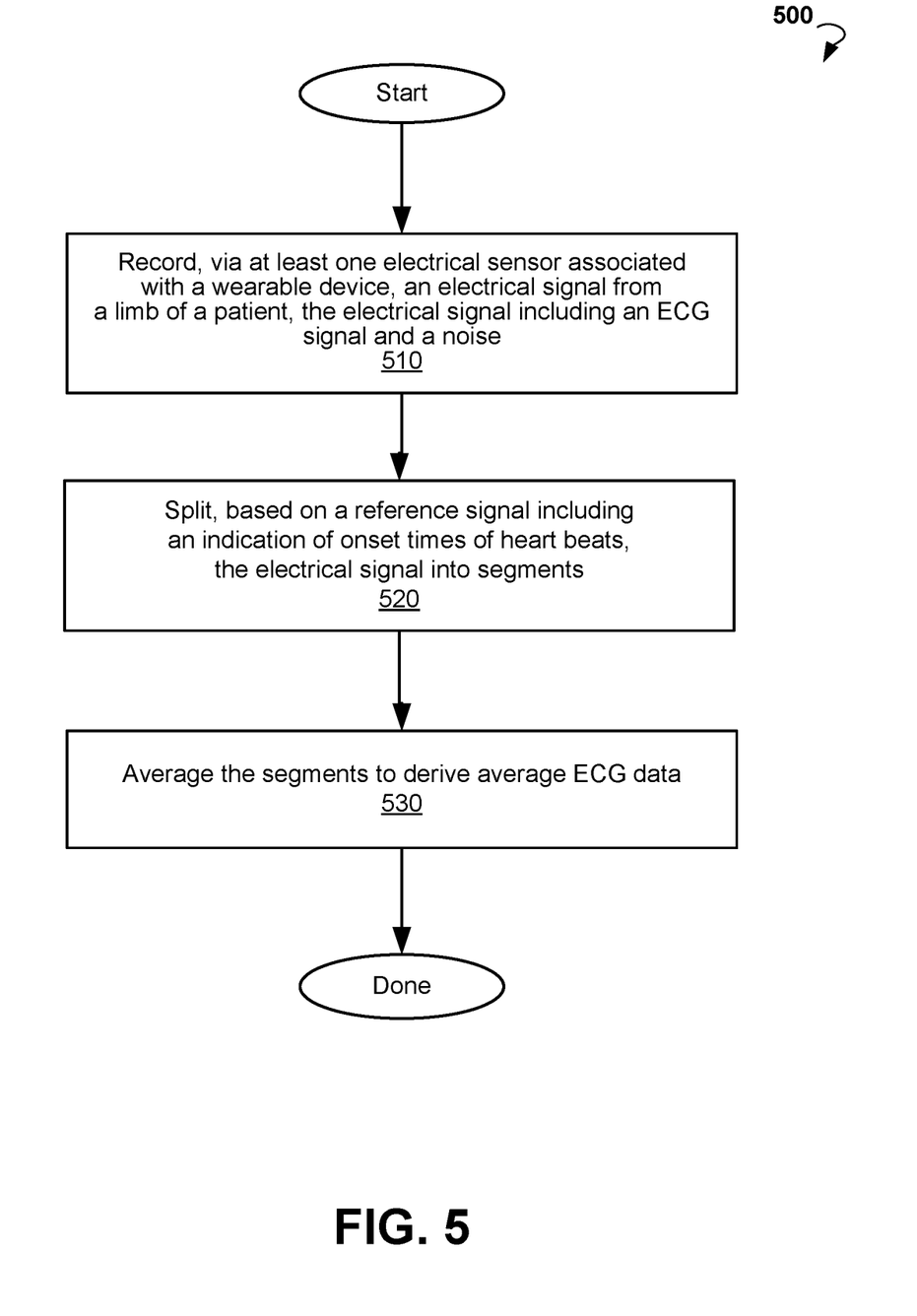
FIG. 5 is a flow chart showing an example method for measuring ECG data using the wearable device.

FIG. 5 is a flow chart of a method 500 for measuring ECG data from using a wearable device, according to an example embodiment. In block 510, method 500 includes recording an electrical signal from a wrist of a patient. The electrical signal can be recorded by at least one electrical sensor associated with the wearable device. The wearable device can be carried out in a shape of a watch, a bracelet, or a wristband configured to be worn on the wrist of the patient. The electrical signal includes an ECG signal and a noise.

In block 520, the method 500 can include splitting the electrical signal into segments based on a reference signal.

The reference signal can include an indication of onset times of heart beats. In some embodiments, the reference signal includes a PPG signal recorded via an optical sensor associated with the wearable device simultaneously with the electrical signal. In certain embodiments, the reference signal is the first derivative of a PPG signal recorded via the optical sensor simultaneously with the electrical signal. The optical sensor can be configured to measure color of skin beneath a pulsating artery of the wrist.

In block 530, the method 500 proceeds to average the segments and to derive average ECG data. Averaging the segments improves the SNR in the electrical signal.

EXAMPLE

Figure 6:
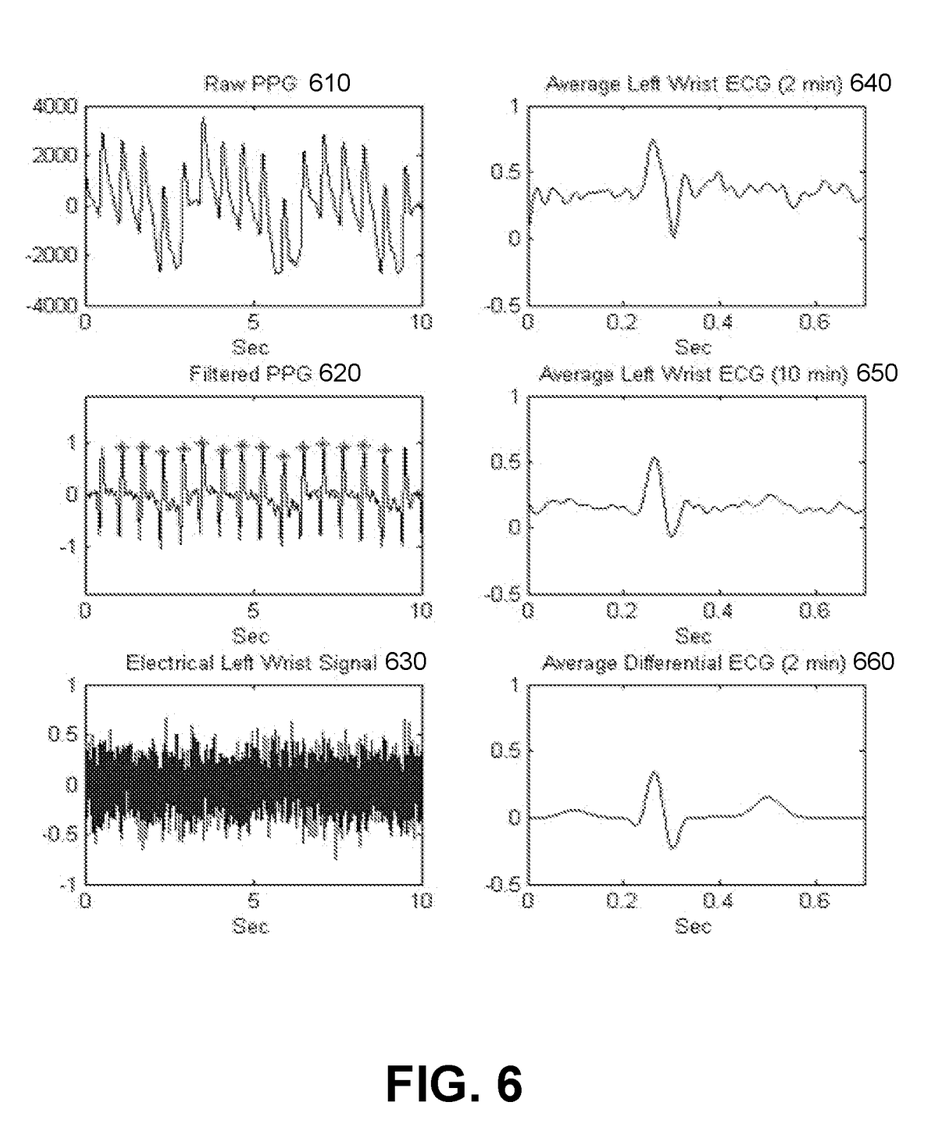
FIG. 6 shows example plots of a raw PPG signal, a filtered PPG signal, an electrical signal from the left wrist, average ECG fata from the left wrist, and average differential ECG data.

FIG. 6 illustrates plots of a raw PPG signal (optical signal) 610, a filtered PPG signal 620, an electrical signal 630, average ECG signals 640 and 650, and an average differential ECG signal 660. Recordings of the electrical signal 630 and a raw PPG signal 610 can be simultaneously measured at a wrist of a patient. The electrical signal 630 can be measured using a differential amplifier, and the optical signal can be measured with a photodiode detector placed beneath the radial artery. The raw PPG (optical) signal 610 can be processed to receive filtered PPG signal 620, yielding trigger points for the time-locked averaging of the ECG signal.

According to example measurements, an average 5 minute ECG signal and 15 minute average ECG signal are shown to converge to a two-sided average ECG signal. The two-sided average ECG signal is measured from both sides (for example, from two different wrists of patient). The ECG complex is already evident in a 5 minute average, yet a 15 minute recording provides a higher quality average waveform.

The present technology is described above with reference to example embodiments. Therefore, other variations upon the example embodiments are intended to be covered by the present disclosure.

What is claimed is:

1. A wearable device for extracting an average electrocardiogram (ECG) waveform, comprising:
    means for recording, via at least a first input plate placed in contact on a single wrist and a second input plate, placed in contact with an opposite side of the single wrist, of at least one electrical sensor associated with the wearable device, an electrical signal from the single wrist of a patient, the electrical signal including an ECG component and a noise component;
    means for detecting a pulse of the patient and recording a photoplethysmogram (PPG) signal, via a PPG optical sensor associated with the wearable device, the electrical signal and the PPG signal being simultaneously measured at the single wrist of the patient;
    means for generating, from the recorded electrical signal, electrical signal segments of the recorded electrical signal, the electrical signal segments being time-locked to the PPG signal by utilizing the PPG signal as a reference signal; and
    means for summing the electrical signal segments in a given time period and dividing by a number of segments to produce an average ECG waveform based on a subset of the electrical signal segments, resulting in a reduction of an uncorrelated noise component of the electrical signal and an extraction of the average ECG waveform from the electrical signal during the time period.

2. The wearable device of claim 1, wherein the PPG optical sensor is further operable to measure a color of skin above a pulsating artery of the single wrist.

3. The wearable device of claim 2, wherein the reference signal is recorded via the PPG optical sensor simultaneously with the electrical signal.

4. The wearable device of claim 2, wherein the reference signal is a first derivative of a PPG signal recorded via the PPG optical sensor simultaneously with the electrical signal.

5. The wearable device of claim 1, further comprising means for detecting changes in the average ECG waveform over time.

6. The wearable device of claim 1, wherein the electrical sensor includes the first input plate configured to be located at an inner side of the single wrist and the second input plate configured to be located at an outer side of the single wrist.

7. The wearable device of claim 1, wherein the reference signal includes indications of onset times of heart beats of the patient.

8. The wearable device of claim 1, wherein the wearable device is carried out in a shape of one of the following: a wristband, a watch, and a bracelet configured to be worn on the single wrist.

9. The wearable device of claim 1, further comprising:
    means for analyzing average ECG waveforms derived over a period of time to determine trends in parameters of the average ECG waveforms, wherein the period of time includes a pre-determined number of one or more of the following: weeks, months, and years;
    means for determining, based at least on the trends, at least one possible symptom or a probable progression of at least one chronic heart disease; and
    means for providing reports and warning messages regarding the at least one possible symptom and the probable progression.

10. The wearable device of claim 1, wherein the electrical signal segments are of a length of an interval between two subsequent heart beats.

11. The wearable device of claim 1, wherein each of the electrical signal segments correspond to one RR interval, which represents an interval between two successive heart beats of the patient.

12. The wearable device of claim 1, wherein summing of the electrical signal segments in a given time period to produce an average ECG waveform is computed by an equation $$S(t) = \sum_{i=1}^{p} (s_i(t) + e_i(t)),$$

wherein p is a number of segments $T_i$ selected for averaging, $s_i(t)$ is an ECG signal and $e_i(t)$ is a noise component.

13. A system for measuring an electrocardiogram (ECG) using a wearable device, the system comprising:
    the wearable device including at least one electrical sensor, the wearable device configured to:
        record, via at least a first input plate placed in contact on a single wrist and a second input plate, placed in contact with an opposite side of the single wrist, of at least one electrical sensor associated with the wearable device, an electrical signal from a single wrist of a patient, the electrical signal including an ECG component and a noise component;
        detect a pulse of the patient and recording a photoplethysmogram (PPG) signal, via a PPG optical sensor associated with the wearable device, the electrical signal and the PPG signal being simultaneously measured at the single wrist of the patient;

generate, by a processor from the recorded electrical signal, electrical signal segments of the recorded electrical signal, the electrical signal segments being time-locked to the PPG signal by utilizing the PPG signal as a reference signal; and sum the electrical signal segments in a given time period and divide by a number of segments to produce an average ECG waveform based on a subset of the electrical signal segments, resulting in a reduction of an uncorrelated noise component of the electrical signal and an extraction of the average ECG waveform from the electrical signal during the time period.

14. The system of claim 13, wherein the PPG optical sensor is further operable to measure a color of a skin above a pulsating artery of the single wrist.

15. The system of claim 14, wherein the reference signal is recorded via the PPG optical sensor simultaneously with the electrical signal.

16. The system of claim 14, wherein the reference signal is a first derivative of a PPG signal recorded via the PPG optical sensor simultaneously with the electrical signal.

17. The system of claim 13, wherein the processor is used to detect changes in the average ECG waveform over time.

18. The system of claim 13, wherein the at least one electrical sensor includes a first input plate configured to be located on an inner side of the single wrist and a second input plate configured to be located on an outer side of the single wrist.

19. The system of claim 13, wherein the processor is part of the wearable device.

20. The system of claim 13, wherein the wearable device is carried out in a shape of one of the following: a wristband, a watch, and a bracelet configured to be worn on the single wrist.

21. The system of claim 13, wherein the wearable device further configured to:

analyze, by the processor, the average ECG waveforms derived over a period of time to determine trends in parameters of the average ECG waveforms, wherein the period of time includes a pre-determined number of one or more of the following: weeks, months, and years;

determine, by the processor and based at least on the trends, at least one possible symptom or a probable progression of at least one chronic heart disease; and provide at least one of a report and a warning message regarding the at least one possible symptom and the probable progression.

* * * * *